United States Patent [19]

Guerrero et al.

[11] Patent Number: 5,609,854
[45] Date of Patent: Mar. 11, 1997

[54] THICKENED AND STABILIZED COSMETIC EMULSION COMPOSITIONS

[75] Inventors: Angel A. Guerrero, Huntington; Thomas C. Klepacky; Pamela C. Asplund, both of Shelton, all of Conn.

[73] Assignee: Elizabeth Arden Company, Division of Conopco, Inc., New York, N.Y.

[21] Appl. No.: 470,515

[22] Filed: Jun. 6, 1995

[51] Int. Cl.$^6$ .................................................. A61K 7/42
[52] U.S. Cl. .......................... 424/59; 423/608; 423/622; 424/60
[58] Field of Search ........................... 424/59, 60

[56] References Cited

U.S. PATENT DOCUMENTS 4,606,914  8/1986  Aronson et al. ........................... 424/59

*Primary Examiner*—Shelley A. Dodson
*Attorney, Agent, or Firm*—Milton L. Honig

[57] ABSTRACT

A cosmetic composition is provided which includes water, an emollient oil, a sunscreen agent and an aluminum salt of a $C_1$–$C_8$ carboxylic acid. Preferred as the aluminum salt is aluminum citrate, the latter not only thickening but also stabilizing the emulsion against breakage.

9 Claims, No Drawings

1

THICKENED AND STABILIZED COSMETIC EMULSION COMPOSITIONS

BACKGROUND OF THE INVENTION

1. Field of the Invention

The invention relates to emulsions containing sunscreens formulated with an improved thickening and stabilization agent, particularly emulsions of the water-in-oil variety.

2. The Related Art

Aqueous cosmetic compositions often require thickeners to achieve an aesthetically pleasing viscosity. Fluids that flow with a watery consistency too rapidly run off the treated skin areas. For a cosmetic to be effective, it often must have substantivity. Thickeners provide this substantivity. Furthermore, low viscosity formulas which may be skin effective nevertheless through their wateriness signal ineffectiveness to the consumer. Products of watery consistency are also aesthetically displeasing to consumers with expectations of rich and creamy products.

Thickening is one but not the only concern when formulating cosmetic emulsions. Phase stability is also of paramount concern. Aqueous and oil phases must be prevented from separating. Gradual loss of viscosity often indicates progressive breakdown of an emulsion.

Certain types of cosmetic ingredients promote emulsion instability. Sunscreen agents are one such class of ingredient. It is difficult to stabilize sunscreen agent containing emulsions, especially water-in-oil emulsions, when seeking systems thickened to an aesthetically pleasing viscosity.

Accordingly, it is an object of the present invention to provide thickened cosmetic sunscreen compositions of sufficiently aesthetically pleasing viscosity.

It is another object of the present invention to provide thickened cosmetic sunscreen compositions stabilized against emulsion breakage and maintainable at substantially constant viscosity.

Still another object of the present invention is to provide a thickened cosmetic sunscreen composition in the form of a water and oil emulsion that exhibits improved aesthetics when applied to the skin.

Yet another object of the present invention is to provide a thickened cosmetic sunscreen composition that maximizes the sun protection factor while minimizing the level of sunscreen agent.

These and other objects of the present invention will more readily become apparent from the description and examples which follow.

SUMMARY OF THE INVENTION

A cosmetic composition is provided which includes:

(i) from about 1 to about 99% by weight of water;

(ii) from about 0.1 to about 30% by weight of an emollient oil;

(iii) from about 0.1 to about 30% of a sunscreen agent active in the ultraviolet radiation range from about 290 to 400 nm; and (iv) from about 0.1 to about 5% by weight of an aluminum salt of a $C_1$–$C_8$ carboxylic acid.

DETAILED DESCRIPTION

Now it has been discovered that aluminum salts of $C_1$–$C_8$ carboxylic acids, especially aluminum citrate, can not only thicken water and oil emulsions but also stabilize the emulsion against breakdown. Improvements in sun protection factor (SPF) may also be achieved through the use of aluminum salts of carboxylic acids.

Cosmetic compositions of the present invention will be emulsions containing a water and an oil phase, particularly a water-in-oil emulsion. Water constituting the aqueous phase will be present in an amount from about 1 to about 90%, preferably from about 30 to 80%, optimally 45 to 70% by weight.

Emollient oils will form the oil phase of emulsions according to the present invention. These emollient oils may be in the form of hydrocarbons, silicones, synthetic or natural esters and combinations thereof. Amounts of the emollient oil will range from about 0.1 to about 30%, preferably from about 0.5 to about 10%, optimally from about 0.5 to about 3% by weight.

Hydrocarbons may be in the form of mineral oil, terpenes (such as squalene), isoparaffins and petroleum jelly.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms. Linear volatile silicone materials generally have viscosities less than about 5 centistokes at 25° C. while cyclic materials typically have viscosities of less than about 10 centistokes. Examples of commercially available volatile silicone oils are Dow Corning® 344 and Dow Corning® 345.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25 ° C.

Silicone copolyols are particularly useful as emollient and emulsifying materials within the context of the present invention. Particularly preferred is Dow Corning® 3225C fluid, a mixture of cyclomethicone and dimethicone copolyol having viscosity at 25° C. of 600–2000 cps and a specific gravity of about 0.963.

Among the ester emollients are:

(1) Alkenyl or alkyl esters of fatty acids having 10 to 45 carbon atoms. Examples thereof include isoarachidyl neopentanoate, isononyl isononanoate, oleyl myristate, oleyl stearate, octyl stearate, oleyl oleate, isononyl octanoate, octyl isononanoate and arachidyl erucate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Mono-, Di- and Triglyceride esters such as PEG-8 caprylic/capric triglyceride.

(6) Sterols esters, of which cholesterol fatty acid esters are examples thereof.

An essential element of the compositions according to the present invention is that of an aluminum salt of a $C_1$–$C_8$ carboxylic acid. Illustrative are the aluminum salts of citric acid, lactic acid, glycolic acid, malic acid, malonic acid, succinic acid, adipic acid, tartaric acid, oxydisuccinic acid, citraconic acid, maleic acid, fumaric acid, pyruvic acid, ascorbic acid, isocitric acid, crotonic acid, pivalic acid and combinations thereof. Most preferred is aluminum citrate. Amounts of the aluminum salt may range from about 0.1 to about 5%, preferably from about 0.2 to about 1%, optimally from 0.25 to 0.4% by weight.

Sunscreen agents are also included in compositions of the present invention. These agents may either be organic or inorganic materials. Illustrative inorganic actives are such materials as microfine titanium dioxide, zinc oxide, polyethylene and various other polymers all of whom when incorporated into a cosmetic composition will protect against ultraviolet light in the range from 290 to 400 nm. The organic sunscreen agents will have at least one chromophoric group absorbing within the ultraviolet range so as also to prevent penetration of 290 to 400 nm radiation penetrating to the skin. Chromophoric organic sunscreen agents may be divided into the following categories (with specific examples) including: p-Aminobenzoic acid, its salts and its derivatives (ethyl, isobutyl, glyceryl esters; p-dimethylaminobenzoic acid); Anthranilates (o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naptholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone, 4-Isopropyldibenzoylmethane, Butylmethoxydibenzoylmethane, Etocrylene and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid and mixtures thereof.

Suitable commercially available organic sunscreen agents are those identified under the following table.

TABLE I

| CTFA NAME | TRADE NAME | SUPPLIER |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Humko Chemical |
| Menthyl anthranilate | DERMOBLOCK MA | Alzo, Inc. |
| Octocrylene | UVINUL N-539 | BASF Chemical Co. |
| Octyl dimethyl PABA | Escalol 507 | ISP - Van Dyk |
| Octyl methoxycinnamate | PARSOL MCX | Bernel Chemical |
| Octyl salicylate | DERMOBLOCK US | Alzo, Inc. |
| PABA | PABA | National Starch |
| 2-Phenylbenzimidazole-5-sulphonic acid | EUSOLEX 232 | EM Industries |
| TEA salicylate | NEO HELIOPAN, Type TS | Haarmann & Reimer |
| 2-(4-Methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BSF Chemical Co. |

Amounts of the aforementioned sunscreen agents will generally range from about 0.1 to about 30%, preferably from about 2 to about 20%, optimally from about 4 to about 10% by weight.

Optionally there may be present in the cosmetic emulsion compositions of the present invention a variety of other materials. Examples include fatty acids, humectants, thickeners/viscosifiers, surfactants, preservatives, biologically active materials and other adjunct ingredients. These are described more fully below.

Fatty acids having from 8 to 30 carbon atoms may be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may be included in the compositions of this invention. The humectant aids in increasing the effectiveness of the emollient, reduces scaling, stimulates removal of built-up scale and improves skin feel. Typical polyhydric alcohols include glycerol (known also as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Surfactants may be included in the compositions of this invention. Total concentration of the surfactant will range from about 0.1 to about 40%, preferably from about 1 to about 20%, optimally from about 1 to about 5% by weight of the total composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from about 2 to about 100 moles of ethylene oxide or propylene oxide per mole of hydrophobe; the $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–C20 fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates and combinations thereof.

Compositions of the present invention may also contain $C_1$–$C_{20}$ α-hydroxycarboxylic acids and salts thereof. The salts are preferably alkalimetal, ammonium and $C_1$–$C_{12}$ alkanolammonium salts. Illustrative acids are glycolic acid, lactic acid and 2-hydroxycaprylic acid. Most preferred is a combination of glycolic and 2-hydroxycaprylic acids and their ammonium salts. Levels of these materials may range from about 0.01 to about 15%, preferably from about 0.1 to about 9%, optimally between about 0.5 and about 7% by weight of the cosmetic composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, imidazolidinyl urea (commercially available as Germall 115®), sodium dehydroacetate and benzyl alcohol.

The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be present in the cosmetic compositions. These ingredients include vitamins (such as Vitamin $B_6$, Vitamin C, ascorbyl palmitate, Vitamin A palmitate, Vitamin E acetate, biotin, niacin and DL-panthenol), amino acids (such as glycine and serine), ceramides (such as Ceramide I and Ceramide III), biohyaluronic acid (with oligosaccharides, available as Actiglide J® Special from Active Organics US) and sodium PCA.

Natural vegetable materials from renewable resources are often desirable in cosmetic compositions. For instance, cosmetic compositions of the present invention may include 62-glucan derived from oats, commercially available under the trademark Microat CP from Nurture Inc., Missoula, Mont. Another natural material is plant pseudocollagen commercially available from Brooks, Inc., South Plainfield, N.J. Amounts of each of the foregoing materials may range from about 0.001 to about 10%, preferably from about 0.05 to about 1%, optimally between about 0.1 and 0.5% by weight.

Colorants, fragrances, opacifiers and abrasives may also be included in compositions of the present invention. Each of these substances may range from about 0.05 to about 5%, preferably between 0.1 and 3% by weight.

Additional thickening agents may include electrolytes such as sodium chloride, aluminum stearate gels and combinations thereof. Amount of the electrolyte may range anywhere from 0.1 to 20%, preferably from about 1 to about 5% by weight. The aluminum stearate gel may be formed from a combination of organic $C_4$–$C_{50}$ ester and aluminum stearate formed as a pregel mix in relative ratios of 10:1 to 1:10, preferably 4:1 to 1:4 by weight.

The following Examples will more fully illustrate the embodiments of this invention. All parts, percentages and proportions referred to herein and in the appended claims are by weight unless otherwise indicated.

EXAMPLE 1

A water-in-oil cosmetic composition with sunscreen active typical of the present invention is illustrated below.

| INGREDIENT | WEIGHT % |
| --- | --- |
| Dow Corning 3225C ® | 14.00 |
| Parsol MCX ® | 6.00 |
| Aluminum Stearate Gel | 5.00 |
| Sodium Chloride | 3.00 |
| Butylene Glycol | 2.50 |
| Actiglyde J ® Special | 2.20 |
| Glycerin | 1.50 |
| Squalene | 1.28 |
| Cetyl Dimethicone | 1.00 |
| Urea | 1.00 |
| Sodium Lactate Solution | 1.00 |
| Silicone Fluid 344 | 0.70 |
| Glycine | 0.50 |
| Sodium PCA | 0.50 |
| Methyl Paraben | 0.30 |
| Chitosan Lactate | 0.20 |
| Tocopheryl Acetate | 0.20 |
| Cetyl Dimethicone Copolyol | 0.20 |
| Aluminum citrate | 0.30 |
| Glydant DMDM ® | 0.20 |
| Colorant | 0.13 |

-continued

| INGREDIENT | WEIGHT % |
| --- | --- |
| Disodium EDTA | 0.10 |
| Plant Pseudocollagen | 0.10 |
| Propyl Paraben | 0.10 |
| Ceramide III | 0.07 |
| Fragrance | 0.05 |
| Ascorbyl Palmitate | 0.02 |
| Beta Glucan | 0.01 |
| Hydroxycaprilic Acid | 0.01 |
| L-Serine | 0.01 |
| Ceramide (1) | 0.0001 |
| Water | to 100 |

EXAMPLE 2

The cream (water-in-oil emulsion) of Example 1 was evaluated with a variety of different salts replacing aluminum citrate. These replacements are listed in Table II below.

TABLE II

| | STABILITY (WEEKS EMULSION STABILITY) | |
| --- | --- | --- |
| ALUMINUM SALT | 50° C. | Cycling 4°–43° C. |
| Aluminum Citrate | 12+ | 12+ |
| Zinc Citrate | 3 | — |
| Magnesium Citrate | — | 1 |
| Aluminum Chloride | 3 | — |
| Aluminum Ammonium Sulphate | 7 | — |
| Aluminum Sulphate | 8 | — |
| Aluminum PCA* | 8 | — |
| Aluminum Formate | 1 | — |
| None | — | 10 |

*PCA = Pyrrolidone Carboxylic Acid

Stability was measured on two separate identical samples. One of the samples was stored at 50° C. and the other was alternately cycled between 4° C. and 43° C. each 24 hours. Completion of the test was at 12 weeks.

Only aluminum citrate (0.3%) allowed the base formulation to maintain stability over the three full 12 weeks both at the 50° C. storage and at the alternating cycling temperature. Other aluminum salts such as aluminum sulphate, aluminum ammonium sulphate and aluminum chloride did not provide sufficient stability to pass the test over the 12 week period. The criticality of aluminum was demonstrated by magnesium citrate which when incorporated into the base formulation did not adequately stabilize the emulsion.

EXAMPLE 3

This example illustrates a cosmetic composition according to the present invention, featuring a combination of UVA and UVB active suncreens.

| INGREDIENT | WEIGHT % |
| --- | --- |
| Dow Corning 3225C ® | 25.0 |
| Parsol 1789 ® | 5.0 |
| Parsol MCX ® | 5.0 |
| Dipropylene Glycol | 4.5 |
| Cetyl Dimethicone Copolyol | 4.5 |
| Glycerin | 2.0 |
| Aluminum citrate | 1.0 |
| Disodium EDTA | 0.2 |
| Methyl Paraben | 0.2 |
| Propyl Paraben | 0.1 |
| Water | to 100 |

EXAMPLE 4

This example illustrates a cosmetic composition according to the present invention, featuring a combination of inorganic active sunscreens.

| INGREDIENT | WEIGHT % |
| --- | --- |
| Dow Corning 3225C ® | 15.0 |
| Cetyl Dimethicone Copolyol | 10.0 |
| Micronized Titanium Dioxide | 7.0 |
| Micronized Zinc Oxide | 7.0 |
| Butylene Glycol | 3.5 |
| Glycerin | 2.5 |
| Aluminum Citrate | 0.8 |
| Disodium EDTA | 0.2 |
| Methyl Paraben | 0.2 |
| Propyl Paraben | 0.1 |
| Water | to 100 |

EXAMPLE 5

This example illustrates a cosmetic composition according to the present invention, featuring a variety of aluminum salts of carboxylic acids.

| | WEIGHT % | | | | |
| --- | --- | --- | --- | --- | --- |
| INGREDIENT | 4A | 4B | 4C | 4D | 4E |
| Dow Corning 3225C ® | 20 | 20 | 20 | 20 | 20 |
| Parsol MCX ® | 6 | 6 | 6 | 6 | 6 |
| Butylene Glycol | 3 | 3 | 3 | 3 | 3 |
| Cetyl Dimethicone Copolyol | 2 | 2 | 2 | 2 | 2 |
| Glycerin | 2 | 2 | 2 | 2 | 2 |
| Methyl Paraben | 0.3 | 0.3 | 0.3 | 0.3 | 0.3 |
| Propyl Paraben | 0.1 | 0.1 | 0.1 | 0.1 | 0.1 |
| Aluminum Lactate | 0.5 | — | — | — | — |
| Aluminum Malate | — | 0.5 | — | — | — |
| Aluminum Tartrate | — | — | 0.5 | — | — |
| Aluminum Succinate | — | — | — | 0.5 | — |
| Aluminum Oxydisuccinate | — | — | — | — | 0.5 |

The foregoing description and Examples illustrate selected embodiments of the present invention and in light thereof various modifications will be suggested to one skilled in the art, all of which are within the spirit and purview of this invention.

What is claimed is:

1. A cosmetic composition comprising:
   (i) from about 1 to about 99% by weight of water;
   (ii) from about 0.1 to about 30% by weight of an emollient oil;
   (iii) from about 0.1 to about 30% of a sunscreen agent active in the ultraviolet radiation range from about 290 to 400 nm, the sunscreen agent being selected from the group consisting of zinc oxide, titanium oxide, benzophenone-3, benzophenone-4, benzophenone-6, benzophenone-8, benzophenone-12, butyl methoxy dibenzoyl methane, PABA, octyl dimethyl PABA, octyl methoxycinnamate and combinations thereof; and
   (iv) from about 0.1 to about 5% by weight of an aluminum salt of a $C_1$–$C_8$ carboxylic acid.

2. A composition according to claim 1 wherein the sunscreen agent is an inorganic material selected from the group consisting of zinc oxide, titanium oxide and mixtures thereof.

3. A composition according to claim 1 wherein the sunscreen agent is octyl methoxycinnamate.

4. A composition according to claim 1 wherein the sunscreen agent is selected from the group consisting of benzophenone-3, benzophenone-4, benzophenone-6, benzophenone-8, benzophenone-12, butyl methoxy dibenzoyl methane, PABA, octyl dimethyl PABA, octyl methoxycinnamate and combinations thereof.

5. A composition according to claim 1 wherein the emollient oil is selected from the group consisting of cyclomethicone, dimethicone copolyol and mixtures thereof.

6. A composition according to claim 1 wherein the aluminum salt is aluminum citrate.

7. A composition according to claim 1 wherein the aluminum salt is present in an amount from about 0.1 to about 0.5% by weight.

8. A composition according to claim 1 further comprising from about 1 to about 10% by weight of an aluminum stearate gel.

9. A composition according to claim 1 wherein the composition is a water-in-oil emulsion.

* * * * *